(12) United States Patent
McDonagh et al.

(10) Patent No.: US 8,268,790 B2
(45) Date of Patent: Sep. 18, 2012

(54) DERMATALOGICAL FORMULATIONS

(75) Inventors: Emma Louise McDonagh, Kelso (GB); Rebecca Louise Kanis, Edinburgh (GB)

(73) Assignee: Zindaclin Limited, Cheshire (GB)

( * ) Notice: Subject to any disclaimer, the term of this patent is extended or adjusted under 35 U.S.C. 154(b) by 97 days.

(21) Appl. No.: 12/574,052

(22) Filed: Oct. 6, 2009

(65) Prior Publication Data
US 2010/0173855 A1  Jul. 8, 2010

Related U.S. Application Data

(63) Continuation of application No. 10/432,848, filed as application No. PCT/GB01/05257 on Nov. 28, 2001, now abandoned.

(30) Foreign Application Priority Data

Nov. 28, 2000  (GB) .................................. 0029018.9

(51) Int. Cl.
*A61K 31/70* (2006.01)
*A61K 8/02* (2006.01)
*A61K 33/32* (2006.01)
*A01N 55/02* (2006.01)

(52) U.S. Cl. ........... 514/24; 424/401; 424/642; 514/494

(58) Field of Classification Search ........................ None
See application file for complete search history.

(56) References Cited

U.S. PATENT DOCUMENTS

| | | |
|---|---|---|
| 3,969,516 A | 7/1976 | Stoughton |
| 4,621,075 A | 11/1986 | Fawzi et al. |
| 5,648,389 A | 7/1997 | Gans et al. |
| 5,733,886 A | 3/1998 | Baroody et al. |

FOREIGN PATENT DOCUMENTS

| | | |
|---|---|---|
| EP | 0506207 | 9/1992 |
| WO | 97/15282 | 5/1997 |

*Primary Examiner* — David J Blanchard
*Assistant Examiner* — Rachael E Bredefeld
(74) *Attorney, Agent, or Firm* — Fish & Richardson P.C.

(57) ABSTRACT

Aqueous preparations of substantially equimolor amounts of a zinc salt and clindamycin phosphate form a polymer useful in the topical treatment of acne and rosacea, with very low systemic levels of clindamycin.

9 Claims, 3 Drawing Sheets

DERMATALOGICAL FORMULATIONS

Figure 1:
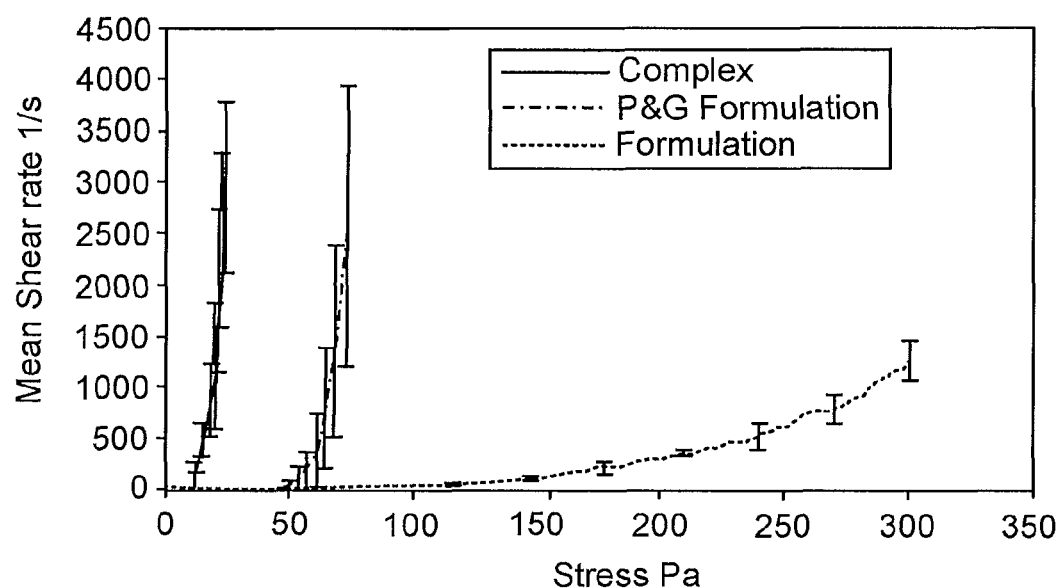

This application is a continuation application of and claims priority to U.S. application Ser. No. 10/432,848, now abandoned, filed on Jan. 28, 2004, which application claims priority under 35 U.S.C. §371 to a national phase filing of international application number PCT/GB01/05257, filed on Nov. 28, 2001, which application claims priority to Great Britain Application No. 0029018.9, filed on Nov. 28, 2000. These applications are incorporated herein by reference.

The present invention relates to dermatological formulations comprising clindamycin and zinc, especially for the treatment of acne or rosacea, to methods of treatment of dermatoses with such formulations, and to methods for preparing such formulations.

Acne vulgaris is a common skin condition that has been reported to affect up to 85% of adolescents. The pathology of the condition is not completely understood, but appears to be associated with the local metabolism of sex hormones during adolescence. This stimulates an increase in the size of the sebaceous glands which, in turn, results in the production of excess sebum. This lipid rich medium provides an excellent growth medium for *Propionibacterium acnes* (*P. acnes*).

Corneocytes retained in the follicular canal, and in the presence of *P. acnes*, block the follicles, with the formation of a hyperkeratotic plug (microcomedo) which frequently, and progressively, enlarges to give rise to the clinically visible comedones, the non-inflammatory lesions characteristic of acne (whiteheads and blackheads).

The anaerobic, lipid rich conditions produced within the follicle after microcomedone formation provide the perfect environment for rapid proliferation of *P. acnes*. Metabolites from this bacterium can then diffuse into the dermis, provoking a T cell/helper cell mediated inflammatory response. This can be further exacerbated by the rupture of the duct and the involvement of certain species of Micrococcaceae.

In itself, acne is not a serious condition. However, given its general, social unacceptability, it can often give rise to severe psycho-social problems, so there is, accordingly, great pressure to find an effective treatment.

Various treatments for acne exist, but are generally hampered by the fact that they are generally unreliable.

A limited number of antibiotics is used to treat acne. In moderate to severe cases, oral treatment may be appropriate, in which case tetracycline, minocycline, doxycycline and erythromycin are commonly prescribed.

For mild to moderate acne, topical preparations are the preferred treatment. Traditionally, benzoyl peroxide has been used but formulations containing erythromycin or clindamycin have become more common. When used alone, either of these compounds has been shown to produce a 50% to 60% reduction in inflammatory lesions.

Zineryt® comprises 4% erythromycin and 1.2% zinc acetate. Studies show that this formulation has a 10% greater efficacy than 2% erythromycin alone, and has become a popular product. However, Zineryt® must be reconstituted by a pharmacist, and only has a shelf-life of five weeks, at room temperature. In addition, it is a runny preparation and uses an alcoholic vehicle. Thus, not only are there problems in application of the lotion to the skin, but alcohol is also a skin drying agent when used as the primary vehicle.

EP-A-506207, to Access Pharmaceuticals, describes the preparation of topical pharmaceutical compositions containing water-soluble, zinc-containing compounds and pharmacologically active agents including, amongst others, the lincomycins as antibacterials. Separately, acne treatment compounds are also disclosed. This document does not disclose derivatives of the pharmacologically active compounds, nor does it address any particular aspect of interaction with zinc, which is there to create a reservoir effect in the skin. The result is to reduce the overall transdermal flux of the active agent, but to enhance the initial uptake of the agent into the dermis where, in association with the zinc, it is retained in the form of a reservoir.

Clindamycin phosphate is a known antibiotic effective in the treatment of acne. Unlike erythromycin, it is not suitable for systemic administration for this indication, but is useful in providing a substance other than erythromycin to treat acne, thereby helping to avoid proliferation of erythromycin resistant strains of bacteria.

Topical clindamycin (Cleocin TÒ Topical Lotion) has been demonstrated to be a safe and effective alternative to oral tetracycline therapy, when applied twice daily for 12 weeks to 43 patients with rosacea [Wilkin et al., Treatment of rosacea: topical clindamycin versus oral tetracycline Int. J. Dermatol. (1993); 32:65-67]. Despite this study, there has been limited development in the use of topical clindamycin to treat rosacea.

U.S. Pat. No. 4,621,075, to Fawzi, discloses combinations of clindamycin phosphate and zinc acetate in a non-aqueous, pharmaceutically acceptable, topical vehicle. The formulations may contain up to 5% water without significant adverse effects on the formation of the desired gels, although no water-containing formulations are exemplified. Diisopropyl sebacate is a required component of this vehicle, the other component preferably being ethanol. The disclosed formulations must be capable of gelling, and it is specifically shown than a 1:1 molar ratio does not gel. In this formulation, diisopropyl sebacate acts as a skin permeation enhancer.

The formulations of U.S. Pat. No. 4,621,075 are very oily to the touch, and do not form clear solutions, with large undissolved particles being left suspended in the final formulation. They are not ideal for the treatment of acne, both because of the oleaginous nature of the skin condition to be treated, and because of the presence of excess ethanol in the formulation. Not only is the greasiness of the formulation not likely to promote good patient compliance, but a greasy formulation is also inappropriate to treat acne. The large amounts of ethanol in the brittle formulation rapidly evaporate to leave a thick oleaginous, or dry, deposit, causing the clindamycin phosphate to come out of solution, and drying out the skin in the process, thereby further enhancing the greasy effect and hindering transdermal adsorption.

WO 97/15282 discloses treatments for dermatological disorders comprising three known types of acne treatment agents: an antimicrobial agent, an alpha or beta hydroxyacid, and a zinc compound.

Surprisingly, we have now found that a stabilised, aqueous preparation of zinc salt and clindamycin phosphate forms a high molecular weight polymer which does not appear to be taken into the skin, thereby reducing flux still further, and which only needs to be applied once a day, by comparison with the twice-daily regimen for other clindamycin products on the market.

Thus, in a first aspect, the present invention provides an aqueous preparation, or formulation, for topical application comprising substantially equimolar amounts of clindamycin phosphate and a water-soluble zinc salt for use in the treatment of dermatoses.

In U.S. Pat. No. 4,621,075, for example, it is noted that the presence of water prevents the formation of the desired gels, with the constituents simply going into solution without gelling.

What we have found is that it is possible to form gels of clindamycin phosphate with zinc salts in the presence of water, provided that a substantially neutral, aqueous preparation of clindamycin phosphate is used. Aqueous solutions of clindamycin phosphate do not form easily. If an alkaline solution is added to the mix of clindamycin phosphate and solvent in an amount suitable to bring the preparation to neutrality, or even slight alkalinity, then a gel will tend to form quickly, on addition of the zinc salt. These gels have superior qualities to the gels disclosed in U.S. Pat. No. 4,621,075.

Thus, in a preferred embodiment, the preparations of the present invention have a substantially neutral pH.

The conditions for gel formation are preferably substantially neutral, preferably between 5.5 and 8.0, and particularly between 7 and 7.5, where gel formation is generally optimal. Once the gel has been formed, then pH may be allowed to vary over a range of substantially neutral pH's, especially between a pH of 5.5 and 8.0, without decomposition. For example, the initial gel may be further, optionally substantially, diluted with other components, such as are discussed below, which may lead to a variation in the pH. In addition, formation of the gel may lead to a drop in pH, as described below. However, provided that such variation does not fall outside of the above range, then the compositions will generally be stable.

The formulations of U.S. Pat. No. 4,621,075 have no pH, as they are non-aqueous, so are unable to provide the stability or gel-forming environment of the present invention.

As noted above, the optimal pH for the formation of the zinc/clindamycin phosphate polymer is around pH 7. Clindamycin phosphate is a zwitterionic compound and, at pH 7, the phosphate group is largely deprotonated, while the tertiary amine is essentially protonated. The phosphate group is, thus, able to complex with the zinc ions of the zinc salt. Increasing or decreasing the pH outside of the above ranges generally leads to the formation of other species and, further, reduces the pharmacological effectiveness of the formulation.

Without being restricted by theory, what we have found is that, essentially, a large, electrostatically bound polymer forms in substantially neutral, aqueous preparations of clindamycin phosphate and zinc salt. These polymers preferably form when the molar amount of zinc salt is approximately equivalent to, or greater than, the amount of clindamycin phosphate. Polymer forms when the amounts of zinc salt and clindamycin phosphate are not equimolar, but the properties of the formulation may be affected by the excess of that constituent present in the greater amount. This is less so with excess zinc salt, but especially where the amount of zinc is much less than equimolar, then any gel formed tends to be thin.

The polymer formed between zinc and clindamycin phosphate does not tend to pass into the skin, and it is likely that the polymer becomes lodged in the stratum corneum. This may well be due to the nature of the polymer itself, but we have also noted that, using in vitro cellulosic membranes, increased levels of zinc further reduce the ability of clindamycin phosphate to penetrate the skin.

When applied to the skin, it appears that clindamycin phosphate, or a complex of clindamycin phosphate and zinc, rapidly becomes adsorbed in the stratum corneum, rather than being absorbed in the dermis, as previously observed in the art for formulations comprising zinc.

More specifically, when such prior art formulations as Dalacin® T are applied to the skin under controlled conditions, while some clindamycin phosphate penetrates the dermis and enters the plasma, most of the clindamycin phosphate remains on the surface of the skin, and is recoverable by swabbing. By contrast, levels of clindamycin phosphate recoverable from the skin, 48 hours after application of a formulation of the invention, drop by as much as 50%. However, whereas with Dalacin® T, clindamycin phosphate is readily detectable in both the dermis and the plasma, formulations of the present invention show little or no clindamycin phosphate present in the dermis, and substantially reduced levels of clindamycin in the plasma.

Accordingly, the formulations of the present invention are advantageous over the art in a number of respects. The aqueous nature of the formulation prevents the skin from drying out, a common problem observed with formulations containing an excess of ethanol. While the zinc is likely to have the reservoir effect of the art, it also serves to bind the clindamycin phosphate as a polymer, so that use of the formulations of the invention results in negligible systemic concentrations of clindamycin phosphate. Further, rather than leave clindamycin exposed on the skin surface, it is rapidly absorbed or adsorbed into the surface layers of the skin, thereby protecting it from being washed off. This is particularly useful, as it mimics the effect of providing much greater levels of clindamycin without the concomitant risk of raising systemic levels. In addition, the formulations of the invention are pleasant to use, and are suitably formulated to be dispensed from a squeezable tube or bottle, for example, as compared to the formulations of U.S. Pat. No. 4,621,075, which tend to be brittle.

The formulations of the present invention comprise a polymeric combination of zinc and clindamycin phosphate which is in a dynamic equilibrium with its constituent parts. Thus, at any given time, zinc and clindamycin phosphate are individually identifiable within the preparation. The amount of complex, or polymer, will vary according to the conditions both in the formulation and on the skin. Application of the formulation to the skin serves to dispense clindamycin phosphate straightaway but, more particularly, the polymer acts as a slow release formulation, dispensing clindamycin phosphate to the skin. Thus, there is both immediate and long term action, which allows the formulations of the present invention to be applied only once daily but, yet, to have the same therapeutic effect as established clindamycin preparations.

The co-ordination complex of clindamycin phosphate and zinc is not dependent on the nature of the anion associated with the zinc in the original zinc salt. As such, the zinc salt used in the present invention is not critical to the invention. However, it will be appreciated that the selected anion should be pharmaceutically acceptable in topical formulations. The salt will be selected from salts of suitable organic or inorganic acids, and is preferably readily soluble in water, or in the solvent mixture used for the dissolution of clindamycin phosphate.

Suitable zinc salts may be selected from those obtainable from both organic and inorganic acids. When the zinc salt is obtained from an organic acid, then it is generally preferred that the acid have a small, readily dissociable anion, such as acetate, propionate or pyruvate, the saturated, lower alkanoic acids and their hydrated forms being preferred, especially zinc acetate and particularly zinc acetate dihydrate. It will be appreciated that the anion is of little or no importance to the polymer, so that the primary consideration is that the zinc salt be able to readily provide the zinc cation, and that the anion not hinder formation of the polymer. It will also be appreciated that the anion should be pharmaceutically acceptable. Similar considerations apply to any inorganic anion selected. Small anions are generally preferable, but larger anions may be selected for their therapeutic activity, for example, as with the organic anions. In general, however, simple anions, such as the chloride, are preferred, with simple organic anions being preferred over the inorganic, as these are more readily soluble in water/cosolvent mixtures.

While the primary means for stabilising the formulations of the present invention is by pH control, other means include the use of anti-crystallising agents such propylene glycol, and thickeners, as discussed further below, as well as diluents and other substances which do not adversely affect the final formulation, or which provide advantages in formulation, such as ethanol. It will be appreciated that all such additional substances, insofar as they form a part of the final formulation, should preferably be pharmaceutically acceptable.

Ethanol, or other hydroxy-substituted hydrocarbon, is suitable to assist in the dissolution of clindamycin phosphate in the original formation of the complex, and is also useful in the preparation of the final formulation. As noted above, clindamycin phosphate is poorly soluble in water and, even in the presence of a suitable base, such as sodium or potassium hydroxide, the compound is not readily soluble. Accordingly, it is preferred to use a co-solvent, such as ethanol, in order to achieve solution.

It will be appreciated that the amount of co-solvent required will be readily determined by those skilled in the art. In general, any amount of co-solvent that enhances dissolution will be useful, and it is preferred to use no more than 70% w/w co-solvent. Suitable alcohols are liquids at room temperature, and are preferably lower alkanols, such as ethanol or isopropanol. The preferred co-solvent is ethanol, as this is pharmaceutically acceptable and readily miscible with water. However, any pharmaceutically acceptable, non-aqueous co-solvent may be employed, provided that it is readily miscible with water.

As it is generally preferred to minimise the amount of co-solvent, in order to minimise any disadvantages, perceived or otherwise, of such co-solvent, then it is preferred to use no more than 50% ethanol overall, and preferably no more than 25%. Formation of the initial complex may involve up to about 60% ethanol, although substantially equal amounts of water and alcohol are preferred.

It will also be appreciated that the amount of co-solvent may be maximised in order to achieve solution, with subsequent removal of all or part of the co-solvent before preparation of the final formulation. The final formulation may simply be the complexed, neutralised clindamycin phosphate and zinc salt in water and co-solvent, or with the co-solvent removed. More preferably, the final formulation comprises further ingredients, such as diluents and/or stabilisers, as discussed below.

Although the polymer formed as the co-ordination complex of zinc and clindamycin phosphate forms a gel under aqueous conditions, it is preferred to use low concentrations of clindamycin phosphate in the topical formulation. Preferred concentrations range from 0.1% to 10%, with more preferred concentrations being from 0.5% to 5%, especially around 1% to 2% by weight. At these concentrations, the gel formed by the interaction of clindamycin phosphate in zinc is not especially strong so that, accordingly, it may be desirable to incorporate a thickener. Suitable thickeners include silicon dioxide, silicates, carbomers and cellulosic compounds, such as hydroxymethylcellulose, hydroxypropylcellulose and hydroxyethylcellulose, with hydroxyethylcellulose being currently preferred. Any other appropriate thickeners may also be used, provided that they do not substantially impede the formation of the zinc/clindamycin phosphate co-ordination complex, and are pharmaceutically acceptable.

Where such thickeners are employed, it is only necessary that they be employed in sufficient quantities to prevent the gel from running. Quantities greater than this may be employed, as desired, in order to achieve the desired consistency.

It is particularly preferred to employ the cellulosic compounds as thickeners or texture modifiers, as these also tend to be able to retain water in the formulation. In addition, the effect on the final formulation is generally to modify the flow characteristics such as to convey pseudoplastic flow character on the formulation, which ensures a pleasing texture on the formulation, and assists in dispensing the formulation, for example.

Amounts of thickeners or congeners may suitably be in the range of about 0.2 to about 8% w/w, although more effective such gellants may be used in lower levels, such as about 0.5 to about 3%, preferably about 0.7 to about 2%, with levels of about 0.8 to about 1.5% being useful, especially in the case of the cellulose derivatives, for example.

As noted above, the preferred pH for forming the polymer is around 7. In the present invention, it is generally preferred to first prepare a solution or suspension of clindamycin phosphate and then to adjust the pH of this preparation to about a pH of 7. More particularly, under the conditions in the accompanying Examples, we have found that pH 7.5 provides good results. Once at this pH, the clindamycin phosphate is completely soluble, especially in the presence of ethanol, for example.

After adjustment to an essentially neutral pH, the zinc salt, such as zinc acetate, is added. This is preferably done after the pH-adjusted solution has been stirred until all of the clindamycin phosphate has dissolved, but this is not necessary. Stirring of this resulting mix leads, generally immediately or within a few minutes, to a thickening of the solution. There is no particular limit as to the type of agitation involved. Stirring is one convenient means, and stirring with high shear, especially in the preparation of large batches, ensures that the resulting gel is homogeneous.

Such formulations can then be used directly, or are preferably diluted to the preferred concentrations, as noted above, together with the incorporation of any preferred excipients, surfactants, colourings, stabilisers, gellants and any other materials which it is desired to incorporate in the final composition.

Thus, the present invention further provides a method for the manufacture of a preparation as described above, comprising first dissolving or suspending clindamycin phosphate in an aqueous vehicle and then adjusting the resulting solution or suspension to a substantially neutral pH, preferably wherein the pH is from pH 7.0 to pH 7.5, inclusive.

There is no particularly preferred alkali, but we find aqueous sodium or potassium hydroxide to be convenient, especially sodium hydroxide. The amount is that which is necessary to bring the aqueous preparation containing the clindamycin phosphate to a pH between 7 and 7.5 or, more generally, a pH from 5.5 to 8.0. The aqueous preparation containing the clindamycin phosphate may be in the form of a solution, suspension, simple mixture, or any combination of these forms. After the alkali has been added, especially to over a final pH of about 6.5, the remaining undissolved clindamycin phosphate rapidly enters solution at ambient temperature in the presence of co-solvent, preferably at least 25% by weight, especially when the co-solvent is ethanol.

When the zinc salt is added to the clindamycin phosphate, complexing of the zinc with the deprotonated phosphate groups results in a neutral polymer but releases protons and the zinc salt anion, so that an acidic solution will tend to form. Where the anion is acetate, for example, then this is not only readily soluble in any water/co-solvent mixture, but also forms less caustic acid solutions in association with protons than inorganic anions, such as chloride, for example.

Thus, the amount of alkali is preferably selected not only to deprotonate the phosphate groups of clindamycin, which preferentially appears to occur at a pH of 7 or above but which, especially depending on conditions, may occur at lower pH's, but also to yield a final formulation having a pH above 5.5, preferably 6.0 or above, after the addition and incorporation of zinc salt.

The term "aqueous vehicle", as used herein, relates to any suitable liquid vehicle comprising a substantial amount of water, preferably at least 30%.

It is generally preferred that this initial preparation of clindamycin phosphate and zinc salt in an aqueous vehicle is used in the preparation of a final formulation. It is also generally preferred that the initial preparation forms less than 50% of the final formulation by weight, with the remainder of the constituents being added after the zinc salt has been added. This allows the polymer to form under optimal conditions, prior to making up to the final formulation.

Indeed, the zinc salt may be added prior to addition of the alkali, or contemporaneously therewith, but this might interfere with the effect on the clindamycin phosphate, and is not generally preferred.

The final formulation should generally be selected so as to not to encourage the decomposition of the polymer. Any dilution of the vehicle containing the initial complex is likely to lead to a certain amount of decomposition, especially if the dilution is with a major proportion of water. Accordingly, it is preferred to use a suitable topical vehicle comprising a significant amount of a non-aqueous vehicle or diluent. In this respect, a significant amount is generally at least 40%, and may be up to about 80% by weight.

Generally, it is preferred to loosely maintain a similar ratio of aqueous:non-aqueous throughout the preparation of both the initial complex and the final formulation. There is no particular ratio that should be observed, but it is preferred to take the solubility of clindamycin phosphate and the zinc salt into account. Clindamycin phosphate is not an especially readily soluble substance even in neat ethanol, while zinc salts, such as the acetate, are readily soluble in water and, to a lesser extent, in ethanol, so that a ratio of about 2:1 non-aqueous:aqueous is generally useful in the final formulation, although a range of about 1:1 to 2.5:1 is also convenient. In particular, the initial preparation of the gel may employ higher quantities of non-aqueous co-solvent. Other ranges will be immediately apparent to the skilled person. The above combinations allow sufficient dissolution of clindamycin phosphate, while maintaining a sufficient quantity of water to encourage zinc ion salvation and interaction with the zwitterionic clindamycin phosphate.

It will also be appreciated that the co-solvents for the final formulation need not necessarily be involved in maintaining clindamycin phosphate in solution, provided that they do not actively drive it out. Instead, they may be involved in other aspects of the formulation, such as described in more detail below. However, it is generally desirable to incorporate a certain level of co-solvent for the purposes of enhancing, encouraging, or maintaining the clindamycin phosphate in solution, and this can suitably form a part of the non-aqueous component of the final formulation.

Thus, it is preferred to employ levels of non-aqueous: aqueous of between 4:1 and 2:3, more preferably 3:1 and 1:1, particularly 2.5:1 and 1.5:1, and especially around 2:1 in both the initial vehicle and the final formulation, the ratio being the same or different, preferably the same for both.

The formulations of the present invention may be in any suitable form, and may be in the form of creams, ointments, lotions, gels or any other suitable form, but are preferably sufficiently viscous not to run off the area of skin to which they are applied and such that an appropriate quantity of the formulation can be applied to the area in question. The aqueous and non-aqueous components may be selected appropriately in order to achieve the desired formulation type. The preferred formulation is a gel.

It is also an advantage of the present invention that it is not generally necessary to use a skin permeation enhancer, such as diisopropyl sebacate. In particular, the presence of such an enhancer leads to greater build up of clindamycin phosphate in the dermis and, inevitably, to greater levels of clindamycin in the plasma. By contrast, this is generally avoided in the formulations of the present invention, especially in the absence of skin permeation enhancers.

We have found that it is advantageous to employ a physical stabilising compound in the present invention. Aqueous formulations of zinc and clindamycin phosphate, after storage, may form crystals, and this is not desirable. Thus, it has been found that it is possible to avoid such crystal formation by the incorporation of agents, such as propylene glycol. Although propylene glycol has been found to be useful in the present invention, any other suitable, hydrophilic solvent which is also pharmacologically acceptable may be used, such as glycerine, or different grades of polyethylene glycols, or macrogols. Such stabilising compounds may be used in any appropriate amount, varying from about 1% by weight to about 80%.

Such hydrophilic solvents, or co-solvents may be employed as substantially the whole of the additional non-aqueous phase of the final formulation, if desired. More preferably, the additional non-aqueous material added to achieve the final formulation contains an amount of any initial co-solvent employed in the preparation of the initial preparation of clindamycin phosphate/zinc complex. This amount may be up to 100%, but is preferably between 10 and 50% of the additional non-aqueous component, and more preferably between 15 and 30%, such as about 20%. Greater amounts may tend to evaporate and concentrate the solution, and this may be undesirable.

Any non-aqueous substance added to achieve the final formulation is preferably non-volatile, or is not so volatile as to substantially completely evaporate, within a short period after application to the skin. In this respect, ethanol may be considered to be volatile, while propylene glycol may be considered to be non-volatile, for example.

Formulations of the present invention have also been found to be thixotropic, and generally increase in viscosity with storage. There is no particular problem with storage, and preferred formulations of the present invention can be stored for at least two years without adverse effects.

Further provided are methods for the treatment of dermatoses comprising application of a pharmacologically effective amount of a formulation as described above. Suitable amounts of formulation to be applied to the skin may comprise about 0.01 to about 0.3 ml cm$^{-2}$, for example, more preferably about 0.05 to about 0.1 ml cm$^{-2}$, but there is no particularly preferred regimen, and it is simply sufficient to apply formulation to the affected area, or the area desired to be treated.

Dermatoses suitable for treatment by the present invention particularly include acne vulgaris, but also include any other conditions treatable by clindamycin or clindamycin phosphate, especially rosacea.

The present invention will now be further illustrated with respect to the following, non-limiting Examples. The materials used in the Examples were sourced as follows: Clindamycin phosphate (USP BN B21946), Genzyme; sodium hydroxide pellets (BN B552682), zinc acetate dihydrate (BN D0325), hydroxyethylcellulose (BN 9906B038), and propylene glycol (BN 08101-1), August Wolff; ethanol (99-100% v/v) and ethanol (96% v/v), BDH; polyethylene glycol 400, Sigma Pharmaceuticals; zinc acetate (anhydrous), Aldrich Chemical Co.; diisopropyl sebacate, A&E Connock Ltd.; and Spectra/Por® Biotech CE membrane (MWCO 5000), NBS Biologicals, Cambs, UK. Deionised water was obtained using an Option 3 Water Purifier (Elga).

Figure 2:
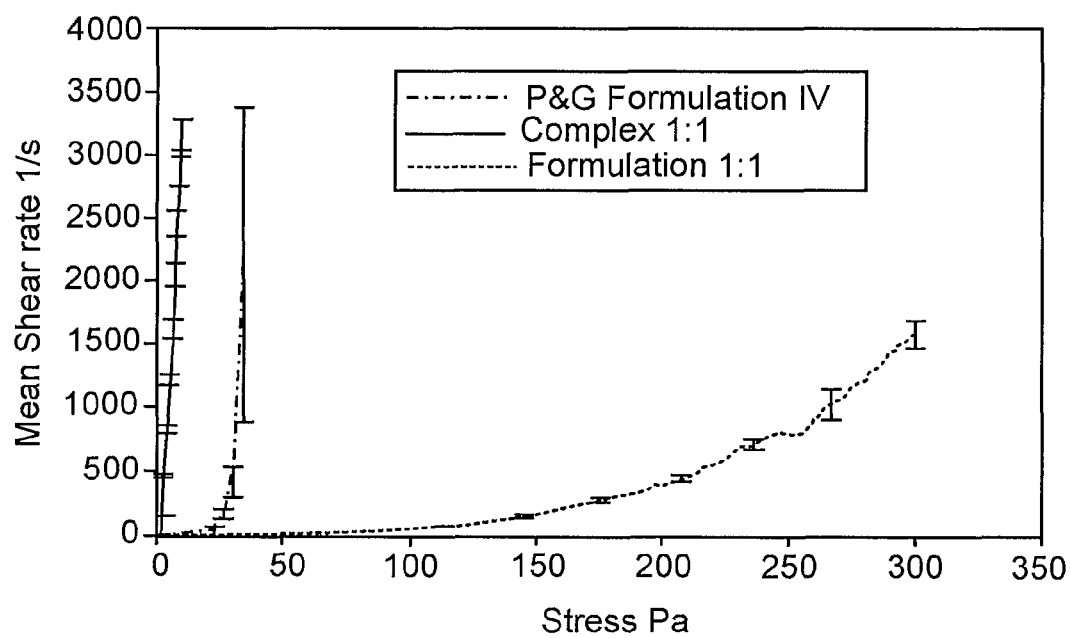
Figure 3:
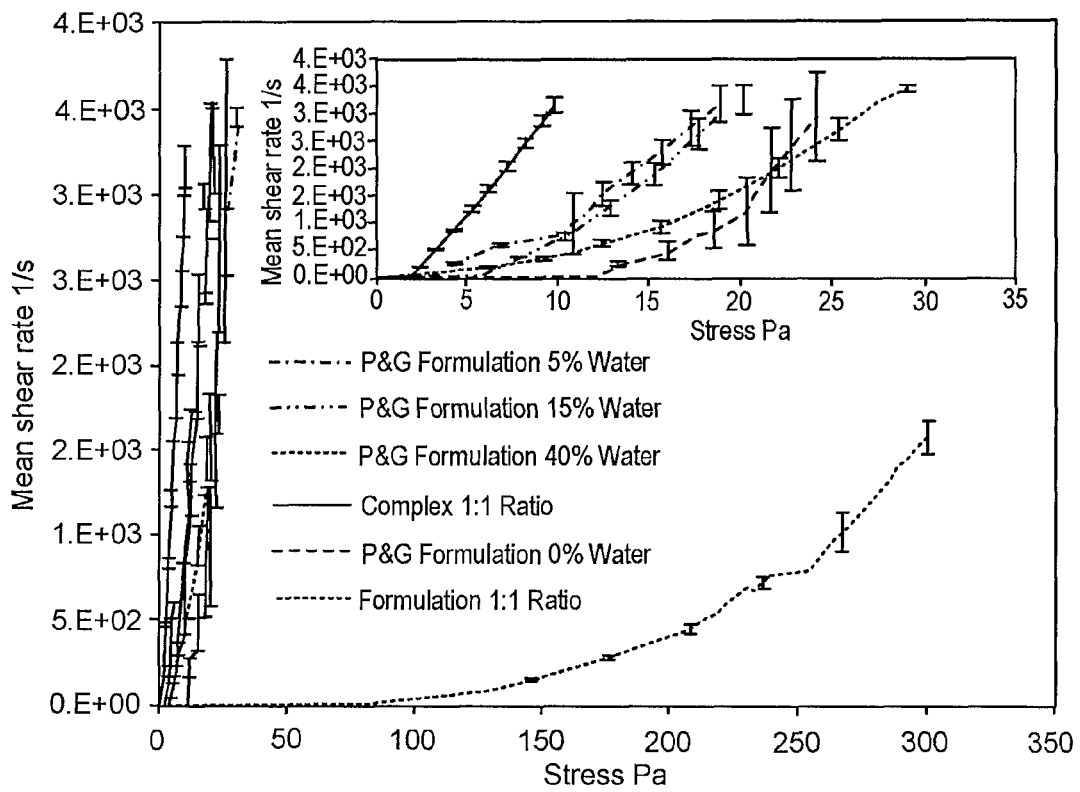
Figure 4:
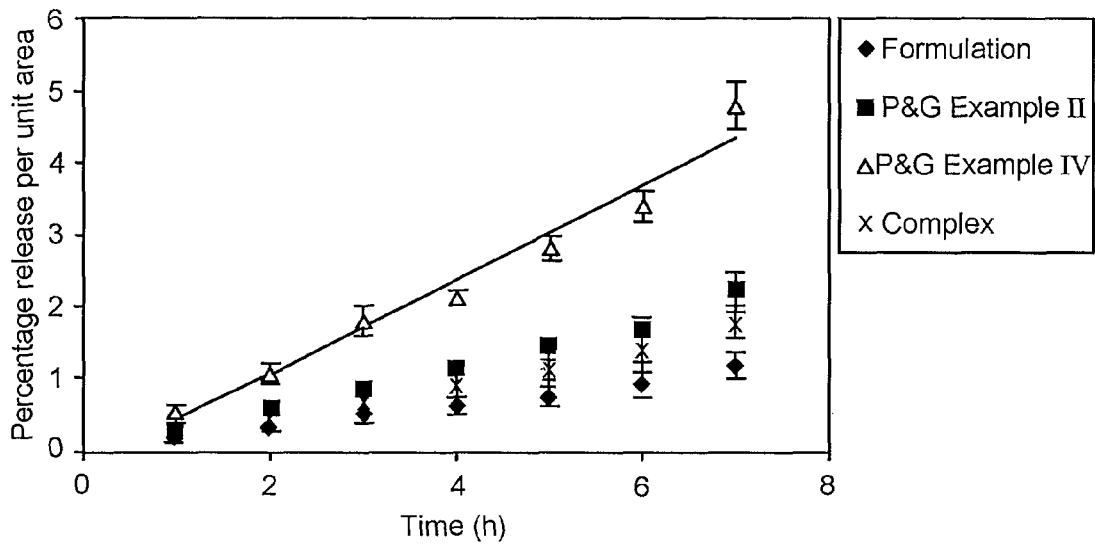
Figure 5:
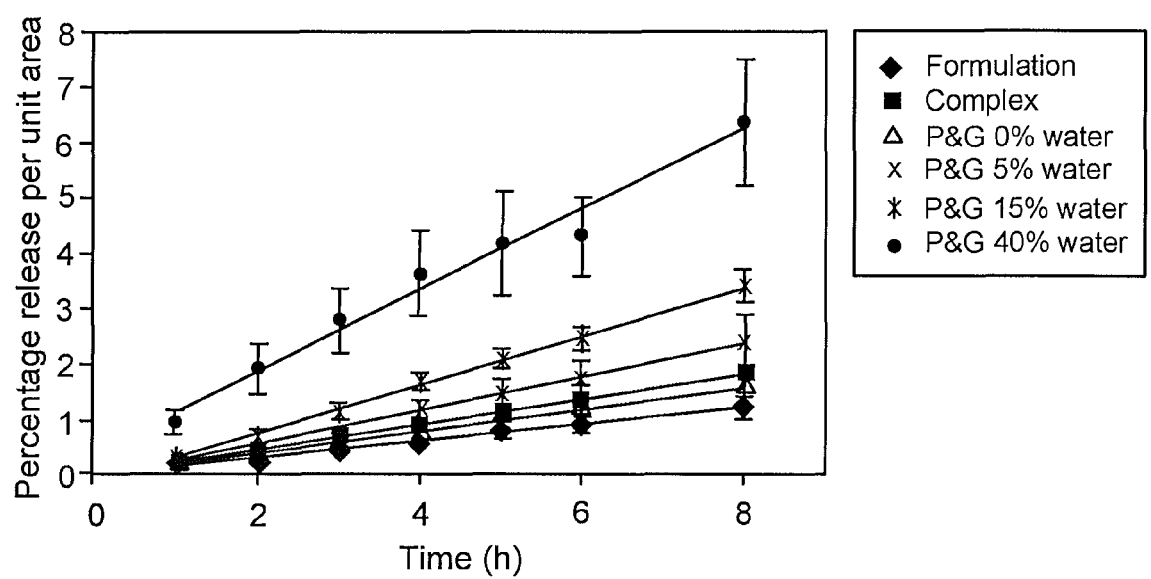

The Examples will be illustrated with respect to the accompanying drawings, in which:

FIG. 1 shows the flow curves representing the behaviour of the formulations having a CP:ZnA molar ratio of 1:1.5;

FIG. 2 shows the flow curves representing the behaviour of formulations from U.S. Pat. No. 4,621,075 examples II and IV, compared with formulations of the present invention;

FIG. 3 shows the flow curves representing the behaviour of the formulations of U.S. Pat. No. 4,621,075, but containing water in amounts between 0 and 40%;

FIG. 4 shows the effect of CP release from P&G II, P&G IV, complex of the invention and formulation of the invention (CP:ZnA, 1:1 molar ratio) over time; and FIG. 5 demonstrates the effect of the addition of water at 5, 15 and 40% to P&G formulations on the release rate of clindamycin phosphate.

EXAMPLE 1

Clindamycin Gel 1% w/w

Method of Preparation
1. Formula
A formula was made up, as shown below:

| Ingredient | Unit Formula (% w/w) |
| --- | --- |
| Complex | |
| Clindamycin phosphate | 1.188[1,2] |
| Purified water | 12.0 |
| Ethanol 96% | 10.0 |
| Sodium hydroxide 30% w/w | q.s. to pH 7.5 |
| Zinc acetate dihydrate | 0.516 |
| Formulation | |
| Hydroxyethylcellulose | 1.0 |
| Propylene glycol | 40.0 |
| Ethanol 96% | 10.0 |
| Purified water | q.s. to 100% |

[1]Equivalent to 1.0% Clindamycin
[2]For convenience this is referred to as Clindamycin 1%
[3]Batch weight corrected for clindamycin phosphate potency 2. Manufacture
Complex
a) Mix ethanol and purified water using a homogeniser.
b) With continuous homogenisation, add the clindamycin phosphate (weight corrected for assay and water content) to form a suspension.
c) While mixing continues, slowly add sodium hydroxide 30% w/w to a pH of 7.5 (allowing clindamycin phosphate to dissolve). Record pH and calculate total amount of water added.
d) Dissolve zinc acetate dihydrate in purified water and mix until a clear solution is formed.
e) With continuous homogenisation add the zinc acetate solution to the pH 7.5, clindamycin phosphate solution. Continue mixing, until a homogeneous, translucent, white gel forms. This process may take place as a number of smaller sub-batches.

Cellulose Gel Base
f) Mix propylene glycol and ethanol 96% until homogeneous.
g) While homogenising, add hydroxyethylcellulose until a clear, homogeneous, gel is formed.

Final Gel Manufacture
h) Add the clindamycin phosphate zinc complex to the base gel and mix until a uniform, white opaque gel is produced.
i) Add water to 100% and mix to homogeneity.
j) Fill into tubes.

EXAMPLE 2

U.S. Pat. No. 4,621,075 discloses combinations of clindamycin phosphate and zinc acetate in a non-aqueous, topical vehicle at a molar ratio greater than 1:12. The patent states that ratios below this result in poor or no gel formation. This Example establishes the differences between the formulations of the present invention and U.S. Pat. No. 4,621,075 (referred to herein as the "P&G patent", or just "P&G"). As used herein, CP is clindamycin phosphate and ZnA is zinc acetate dihydrate.

In contradiction to the patent, it was found that gel formation occurred at CP:ZnA, 1:1 molar ratio. All P&G formulations were very oily to the touch.

The rheology of formulations of the present invention and P&G formulations is studied in this Example. Simple fluids where the rate of flow is directly related to the applied stress can be regarded as Newtonian fluids. However, most pharmaceutical fluids do not follow this law because the viscosity of the fluid varies with the rate of shear and thus are regarded as non-Newtonian fluids. One deviation is plastic flow, which occurs when the flow curve does not pass through the origin, but intersects with the shear stress axis at a point referred to as the yield value. This is because the plastic material does not flow until such a value of shear stress has been exceeded. At lower stresses, the substance behaves as a solid (elastic) material.

Pseudoplastic flow arises at the origin, since no yield value exists and the material will flow as soon as shear stress is applied. However, the slope of the curve gradually increases with increasing rate of shear. The viscosity of pseudoplastic materials is derived from the reciprocal of the linear portion of the flow curve or any tangent drawn to it (as with other substances). Accordingly, viscosity decreases as the shear rate is increased for pseudoplastic materials.

This Example is divided into three parts. In the first, the P&G complex was prepared as described in U.S. Pat. No. 4,621,075, example V, with clindamycin phosphate:zinc acetate molar ratios of approximately 1:0.5, 1:1, 1:1.5 and 1:2, and their rheology compared to those of a preferred formulation of the present invention prepared with similar CP:ZnA ratios. As with the other parts of this Example, the preferred formulation of the present invention was prepared as both the complex and the final formulation.

In the second part of this Example, the P&G formulation was prepared as described in U.S. Pat. No. 4,621,075, examples II and IV, and its rheology compared to that of a preferred formulation of the present invention.

In the third part, the P&G formulation was prepared as described in U.S. Pat. No. 4,621,075, example V, with clindamycin phosphate:zinc acetate molar ratios of 1:1.5, and the effect of 5, 15 and 40% (w/w) water on the rheology of the formulation compared to those of a preferred formulation of the present invention.

Part 1
P&G Formulations 28.0 g diisopropyl sebacate will be weighed into a beaker. 70.5 g ethanol will then be weighed out and added to the beaker. These two components will then be mixed together with moderate agitation using a magnetic stirrer. The beaker will be kept covered during mixing in order to minimise ethanol evaporation. 1.0 g clindamycin phosphate will be added to the beaker and stirring will continue for about two minutes. 0.5 g zinc acetate (anhydrous) will then be added and the stirring will continue until the mixture thickens. The stirring bar will be removed and the mixture will be set aside. After several hours, a clear gel will form.

Molar ratios of clindamycin phosphate:zinc acetate (anhydrous) will be altered by altering the zinc acetate molarity (adjusted with anhydrous ethanol) with the molarity of clindamycin phosphate being kept constant. The clindamycin phosphate:zinc acetate (Molar) ratios examined were: 1:0.5; 1:1.0; 1:1.5; and 1:2.0.

Formulations of the Invention

The complex was prepared as follows. 40 g ethanol and 40 g purified water will be mixed using a homogeniser. With continuous homogenisation, clindamycin phosphate (weight corrected for assay and water content) will be added to form a suspension. While mixing continues, sodium hydroxide 30% w/w will be added to a pH of 7.5 (pH and total amount of water will be recorded). 2.064 g of zinc acetate dihydrate will be dissolved in 8 g of purified water and mixed until a clear solution is formed. With continuous homogenisation, zinc acetate solution will be added to the pH 7.5 clindamycin phosphate solution. Mixing is continued until a homogeneous translucent gel is formed.

The formulation was prepared as follows. 160 g propylene glycol will be mixed with 40 g of ethanol 96% v/v until homogeneous. While homogenising, 4 g of hydroxyethylcellulose will be added until a clear homogeneous gel is formed. The climdamycin phosphate:zinc complex will then be added to the thus formed gel and mixed until a uniform, white opaque gel is produced. Water will be added, until a final weight of 400 g is achieved, and mixed. The molar ratio of clindamycin phosphate:zinc acetate dihydrate will be altered by altering the zinc acetate dihydrate molarity (adjusted with water) with the molarity of clindamycin kept constant.

At completion of the preparation, formulations will be stored at room temperature for 30 minutes prior to the rheology and diffusion studies, which will be performed simultaneously. Such a protocol ensures that all the formulations will be tested at the same age.

| Ingredient | % w/w |
|---|---|
| Complex | |
| Clindamycin phosphate | 1.188 |
| Purified water | 12.0 |
| Ethanol 96% | 10.0 |
| *Sodium hydroxide 30% w/w | qs to pH 7.5 |
| Zinc acetate dihydrate | 0.516 |
| Gel base | |
| Hydroxyethylcellulose | 1.0 |
| Propylene glycol | 40.0 |

| Ingredient | % w/w |
|---|---|
| Ethanol 96% | 10 |
| Purified water | qs to 100% |

*Preparation of 30% (w/v) aqueous sodium hydroxide: 3 g sodium hydroxide will be dissolved in 10 ml water.

Part 2
Formulations of the Invention

These were prepared as in Part 1, above.

P&G Formulations

U.S. Pat. No. 4,621,075 example II—25.0 g polyethylene glycol will be weighed into a beaker. 73.4 g ethanol will then be weighed out and added to the beaker. These two components will then be mixed together with moderate agitation using a magnetic stirrer. The beaker will be kept covered during mixing in order to minimise ethanol evaporation. 1.0 g clindamycin phosphate will be added to the beaker and stirring continued for about two minutes. 0.54 g zinc acetate (anhydrous) will then be added and the stirring will continue until the mixture thickens. The stirring bar will be removed and the mixture will be set aside. After several hours, a clear gel will form.

| Ingredients | % (w/w) |
|---|---|
| Clindamycin phosphate | 1.0 |
| Zinc acid (anhydrous) | 0.54 |
| Polyethylene glycol 400 | 25.0 |
| Ethanol (anhydrous) | 73.46 |

CP:Zn (1:1.5 molar)

U.S. Pat. No. 4,621,075 example IV—99.23 g of ethanol will be weighed out and added to a beaker. 0.50 g clindamycin phosphate will be added to the beaker and stirred for about two minutes. The beaker will be kept covered during mixing in order to minimise ethanol evaporation. 027 g zinc acetate (anhydrous) will then be added and the stirring will continue until the mixture thickens. The stirring bar will be removed and the mixture will be set aside. After several hours, a clear gel will form.

| Ingredients | % (w/w) |
|---|---|
| Clindamycin phosphate | 0.50 |
| Zinc acetate (anhydrous) | 0.27 |
| Ethanol (anhydrous) | 99.23 |

CP:Zn (1:1.5 molar)

Part 3
Formulations of the Invention

These were prepared as in Part 1, above.

P&G Formulations

U.S. Pat. No. 4,621,075 example V—28.0 g diisopropyl sebacate will be weighed into a beaker. 70.46 g, or other amount in accordance with the water content (see Table below) ethanol will then be weighed out and added to the beaker. These two components will then be mixed together with moderate agitation using a magnetic stirrer. The beaker will be kept covered during mixing in order to minimise ethanol evaporation. 1.0 g clindamycin phosphate will be added to the beaker and stirring will continue for about two minutes. 0.54 g zinc acetate (anhydrous) will then be added and the stirring will continue until the mixture thickens. Water (as applicable) will then be added to the mixture and stirring continued until a homogenous mixture is formed. The stirring bar will be removed and the mixture will be set aside. After several hours, a clear gel will form. The molar ratio of clindamycin phosphate:zinc acetate (anhydrous) remains constant whist the addition of water will be replaced by the ethanol content.

| Ingredient | CP:Zn (1:1.5) % (w/w) | CPZn (1:1.5) % (w/w) | CPZn (1:1.5) % (w/w) | CPZn (1:1.5) %w/w) |
|---|---|---|---|---|
| Clindamycin phosphate | 1.00 | 1.00 | 1.00 | 1.00 |
| Zinc acetate | 0.54 | 0.54 | 0.54 | 0.54 |
| Water | 0 | 5.0 | 15.0 | 40.0 |
| Ethanol (anhydrous) | 70.46 | 65.46 | 55.46 | 30.46 |
| Diisopropyl sebacate | 28.0 | 28.0 | 28.0 | 28.0 |

CP:Zn (1:1.5 molar)

Rheology

Rheological measurements were carried out using a Carri-Med CSL100 rheometer with the settings shown in the Table below.
a) 2 mL of formulation to be studied was expelled from a syringe (5 ml) at an approximate rate of 1 ml/s.
b) The sample was then gently placed on the centre of the platform using a spatula
c) The instrument was used in a shear stress mode to produce flow curves.
d) The number of replicates measured for each formulation were dependent upon the time required to complete each flow curve.

| 1. | Preshear stress | 0 Pa |
| 2. | Preshear time | 00:00:00 HH:MM:SS |
| 3. | Equilibration time | 00:01:00 HH:MM:SS |
| 4. | Experimental mode | shear stress sweep |
| 5. | Temperature | 15.0° C. |
| 6. | Start Stress | 0 Pa |
| 7. | *End Stress | 10.00 Pa |
| 8. | Stress mode | linear |
| 9. | *Ascent time | 00:05:00 HH:MM:SS |
| 10. | Measurement system type | parallel plate |
| 11. | Plate diameter | 4.0 cm |
| 12. | Measurement system gap | 250 μm |
| 13. | Measurement system inertia | 1.440 μNms$^2$ |

*The end stress and ascent time were altered depending on the nature of the formulation however, a stress application rate of 2 Pa/min was maintained throughout the experiment for all formulations.

Results

No gel prepared in accordance with example V of U.S. Pat. No. 4,621,075 was clear, all gels containing undissolved CP.

Rheology Studies

At a CP:ZnA molar ratio of 1:0.5, the flow curves of both the complex of the invention and P&G formulation were indicative of plastic flow, whilst the flow curve of the formulation of the invention was typical of pseudoplastic flow. These observations were found to be similar for all other CP:ZnA molar ratios investigated, and are illustrated in FIG. 1, for a CP:ZnA molar ratio of 1:1.5. As the CP:ZnA molar ratio was increased from 1:0.5 to 1:1.5, the yield value of the complex of the invention and the P&G formulation were observed to increase. However, no significant difference ($p>0.05$) in yield value was observed between molar ratios of 1:1.5 and 1:2 for both the systems.

In the accompanying FIG. 1, the flow curves representing the behaviour of the formulations having a CP:ZnA, 1:1.5 molar ratio are shown. As in other Figures, "Complex" and "Formulation" indicate the complex and the formulation of the invention, respectively.

From the results in Table 1, it was clearly demonstrated that the formulation with the highest $\eta_{app}$ was obtained with all the molar ratios of CP:ZnA in the formulation of the invention. The $\eta_{app}$ (apparent viscosity—derived from the reciprocal of the slope of the curve) was also observed to increase as the molarity of ZnA was increased from 0.5 to 2.0 for all formulations investigated (with the exception of the P&G formulation at CP:ZnA 1:2 molar ratio). No obvious trend was observed when the P&G formulation was compared to the complex of the invention. At a CP:ZnA molar ratio of 1:0.5, the $\eta_{app}$ of the complex of the invention was found to be significantly ($p<0.05$) greater than the P&G formulation. However, although the $\eta_{app}$ of the P&G formulation was found to be greater than the complex of the invention at all other molar CP:ZnA ratios, no significant ($p>0.05$) difference was observed.

TABLE 1

The mean apparent viscosity ($\eta_{app}$) determined from the reciprocal of the gradient obtained from the linear region of the flow curves.

| Formulation | $\eta_{app}$ (Pas) Mean ± s.d. (n = 2 to 6) | P value compared to Formulation of the invention |
|---|---|---|
| CP:ZnA (1:0.5) | | |
| P&G formulation | 0.0017 ± 0.0001 | P < 0.05 |
| Complex of the invention | 0.0021 ± 0.00003 | P < 0.05 |
| Formulation | 0.0338 ± 0.0031 | |
| CP:ZnA (1:1) | | |
| P&G formulation | 0.0029 ± 0.0005 | P < 0.05 |
| Complex of the invention | 0.0024 ± 0.0001 | P < 0.05 |
| Formulation | 0.0581 ± 0.00154 | |
| CP:ZnA (1:1.5) | | |
| P&G formulation | 0.0056 ± 0.0036 | P < 0.05 |
| Complex of the invention | 0.0025 ± 0.0002 | P < 0.05 |
| Formulation | 0.0699 ± 0.0052 | |
| CP:ZnA (1:2) | | |
| P&G formulation | 0.0042 ± 0.0017 | P < 0.05 |
| Complex of the invention | 0.0035 ± 0.0002 | P < 0.05 |
| Formulation | 0.1147 ± 0.0214 | |

Part 2

In this part, the flow curves of the complex and formulation of the invention (CP:ZnA, 1:1) and P&G examples II and IV were compared. As previously mentioned, the complex and formulation of the invention exhibited plastic and pseudoplastic flow properties, respectively. A flow curve for the P&G example II formulation could not be constructed due to its excessively high yield value (>350 Pa). The flow curve of the P&G example IV formulation suggests significantly ($p<0.05$) greater plastic flow properties compared to the complex of the invention formulation.

The results are shown in FIG. 2, which shows the flow curves representing the behaviour of the formulations investigated.

Table 2 compares the $\eta_{app}$, of the formulations investigated. The $\eta_{app}$ of the P&G example IV formulation was not found to be significantly different ($p>0.05$) to the complex of the invention. However, the formulation of the invention was found to be significantly ($p<0.05$) greater than both the complex of the invention and the P&G example IV formulation.

TABLE 2

The mean apparent viscosity ($\eta_{app}$) determined from the reciprocal of the gradient obtained from the linear region of the flow curves.

| Formulation | $\eta_{app}$ (Pas) Mean ± s.d. (n = 3 to 5) | P value compared to Formulation |
|---|---|---|
| P&G example IV | 0.0018 ± 0.0014 | P < 0.05 |
| Complex, CP:ZnA (1:1) | 0.0024 ± 0.0001 | P < 0.05 |
| Formulation, CP:ZnA (1:1) | 0.0581 ± 0.0015 | |

Part 3

In this part, the flow curves of the P&G formulation (CP:ZnA, 1:1.5) at 5, 15 and 40% (w/w) water, the complex of the invention and formulation of the invention were compared. As previously observed, the complex of the invention and the final formulation exhibited plastic and pseudoplastic flow properties, respectively. Once again, the flow curves of the P&G formulations were found to be indicative of plastic flow. However, no obvious trend in the flow curves was observed on the addition of water to the P&G formulations. The results are shown in FIG. 3, which shows the flow curves representing the behaviour of the formulations investigated. The plastic flow properties of the P&G formulations with 5 and 15% (w/w) water were found to be similar, while the P&G formulations with 0 and 40% (w/w) water also exhibited similar plastic flow properties but having a significantly greater yield value. The flow curves of the P&G formulations investigated were characteristically more plastic compared to the complex of the invention.

Table 3 demonstrates the $\eta_{app}$ of the formulations investigated. Again, the results did not show any obvious trend when the percentage of water was increased to 40% (w/w) in the P&G formulation. No significant difference in the $\eta_{app}$ was observed between P&G formulations with 5% and 15% (w/w) water, and this was found to be similar for 0 and 40% (w/w) water. Importantly, all P&G formulations investigated in this study was found to be significantly (p<0.05) greater in $\eta_{app}$, compared to the complex of the invention (CP:ZnA, 1:1) whilst the $\eta_{app}$ of the formulation of the invention was found to be significantly (p<0.05) greater than all other systems investigated.

TABLE 3

The mean apparent viscosity ($\eta_{app}$) determined from the reciprocal of the linear region of the gradient of the flow curves.

| Formulation | $\eta_{app}$ (Pas) Mean ± s.d. (n = 3 to 5) | P value compared to Formulation |
|---|---|---|
| P&G (CP:ZnA, 1:1.5) 0% water | 0.0056 ± 0.0036 | P < 0.05 |
| P&G (CP:ZnA, 1:1.5) 5% water | 0.0037 ± 0.0003 | P < 0.05 |
| P&G (CP:ZnA, 1:1.5) 15% water | 0.0038 ± 0.0007 | P < 0.05 |
| P&G (CP:ZnA, 1:1.5) 40% water | 0.0048 ± 0.00007 | P < 0.05 |
| Complex of the invention, CP:ZnA (1:1) | 0.0024 ± 0.0001 | P < 0.05 |
| Formulation of the invention, CP:ZnA (1:1) | 0.0581 ± 0.0015 | |

The plastic flow exhibited by the complex of the invention and the P&G formulations in parts 1, 2 and 3 was found to be dependent upon the complexation between CP and ZnA. This was clearly demonstrated in part 1, when the $\eta_{app}$ of the formulations generally increased as the CP:ZnA molar ratio increased from 1:0.5 to 1:2.

The pseudoplastic flow demonstrated for all formulations of the invention at all CP:ZnA molar ratios investigated may be due to the hydroxyethylcellulose present therein. A flow curve for the P&G example II formulation was not constructed, the high yield value of the formulation suggesting a brittle gel structure.

All the P&G formulations investigated exhibited more plastic flow than the complexes of the invention, although no direct comparisons could be made between the formulations of the invention and the P&G formulations as both sets of formulations exhibited different flow properties. This was true even for the P&G formulations which were made with water (contrary to the teachings of U.S. Pat. No. 4,621,075), the presence of water making surprisingly little notable difference to the properties of the P&G formulations.

The results show that zinc substantially affects the rheological properties of complexes of the invention and the P&G formulation, the plastic flow properties being found to increase as the CP:ZnA ratio was increased from 1:0.5 to 1:1.5, although no significant difference was observed between CP:ZnA ratios of 1:1.5 and 1:2 for either formulation. However, all P&G formulations (with the exception of CP:ZnA, 1:0.5) were found to have a significantly higher $\eta_{app}$ when compared to the corresponding complexes of the invention, indicating the presence of different mechanisms in the formulations.

The influence of the CP:ZnA complex was not as significant for the formulations of the invention, the pseudoplastic flow exhibited by the formulations of the invention suggesting that the P&G formulations were significantly different from the formulations of the invention. This was substantiated by the data from part 2. The fact that addition of different amounts of water to the P&G formulation made no difference to the rheological properties of these formulations further suggested that the P&G formulations and the formulations of the invention are significantly different.

Thus, from the rheological data obtained, it could be concluded that both the formulations of the invention and the P&G formulations behave very differently in terms of the mechanisms involved in the complexing of CP with Zn and the resultant effect on the rheology.

EXAMPLE 3

Release Studies

In this Example, release rates of clindamycin from P&G formulations were compared with release rates of formulations of the present invention across a synthetic membrane.

The guidance based on SUPAC-SS for non sterile semisolid dosage forms was followed [ZCG 31T; FDA (CDER), 1997, Guidance for industry—SUPAC-SS Non-sterile Semisolid Dosage Form, Scale-up and post-approval changes: Chemistry, manufacturing and controls; in vitro release testing and in vivo bioequivalence documentation]. This guidance addresses nonsterile semisolid preparations such as creams, gels, lotions and ointments intended for topical routes of administration.

This Example was performed in three parts, and using formulations as prepared in accordance with parts 1, 2 and 3 of Example 2, above.

The pH of all the formulations to be studied was measured at the beginning and end of the experiments. The testing of formulations was conducted in accordance with the FDA's SUPAC In Vitro Release Testing and In Vivo Bioequivalence guidelines (supra).

Six Franz diffusion cell systems (18 mm diameter orifice) system, fitted with a synthetic membrane (cellulose ester MWCO 3500) with deionised water as receiver fluid, were used for each batch. An accurately weighed amount (300 mg) of the formulation, corresponding to an infinite dose condition, was placed uniformly on the membrane and occluded with Parafilm® to prevent solvent evaporation and compositional changes. The Franz cells were placed in a water bath at 32° C. A sample (500 μL) of the receptor phase was removed at 1, 2, 3, 4, 5, 6 and 8 h. Any aliquots removed from the receptor chamber were replaced with fresh aliquot of receiver fluid (deionised water). Samples removed from the receptor phase were analysed for drug content by high performance liquid chromatography (HPLC).

| HPLC Methodology | |
| --- | --- |
| Mobile Phase: | 80:20, pH 2.5 phosphate buffer:acetonitrile |
| Column: | Supelcosil LC-8, 25 cm × 4.6 mm, 5 μm |
| Detector: | 210 nm |
| Flow Rate: | 1.0 mL/min |
| Injection Volume: | 100 μL |
| Temperature: | 35° C. |

Preparation of buffer: potassium phosphate buffer (13.6 mg/mL), pH 2.5, will be prepared by dissolving 68 g of potassium dihydrogen orthophosphate in 4 L of water. The solution will be adjusted to pH 2.5 with orthophosphoric acid and water will be added to 5 L. The buffer will be filtered as required.

Mobile phase: 80 parts by volume pH 2.5 phosphate buffer will be mixed with 20 parts by volume HPLC grade acetonitrile. The mobile phase will be filtered before use.

The percentage release was plotted against time. This yielded a straight line, the slope of which represented the release rate. The six samples yielded six slopes for each formulation, providing in vitro release rates.

The pH's of all the complex and formulations of the invention were determined, and are shown below.

| Formulation | pH before study | pH after study |
| --- | --- | --- |
| Complex (CP:ZnA) | | |
| 1:0.5 | 6.87 | 6.86 |
| 1:1 | 6.06 | 6.04 |
| 1:1.5 | 6.16 | 6.14 |
| 1:2 | 6.19 | 6.17 |
| Formulation (CP:ZnA) | | |
| 1:0.5 | 7.34 | 7.32 |
| 1:1 | 6.25 | 6.23 |
| 1:1.5 | 5.98 | 5.97 |
| 1:2 | 5.97 | 5.97 |

In addition, the pH's of the P&G formulations were taken before testing, and were as follows:

| Formulation | pH before study |
| --- | --- |
| Part 1 (CP:ZnA) | |
| 1:0.5 | (6.3) |
| 1:1 | (5.1) |
| 1:1.5 | (6.1) |
| 1:2 | (5.5) |
| Part 2 (CP:ZnA) | |
| 1:1.5 | (6.2) |
| Part 3 (w/w % water) | |
| 0 | (6.1) |
| 5 | 5.7 |
| 15 | 5.5 |
| 40 | 4.9 |

Figures in brackets indicate no pH, the figure being an apparent pH produced by a pH meter in the absence of water in the preparation.

Part 1

The release profiles of the each of the formulations tested, at all CP:ZnA molar ratios, are shown in Table 4. It can be seen that the different molar ratios of CP:ZnA significantly ($p<0.05$) influence the rate of release of CP from all formulations across the cellulose acetate membrane, but with the formulations of the invention ("Formulation" in the Table below) exhibiting little change. It is notable that the lowest level of release is for the formulation of the invention at a molar ratio of CP:ZnA of 1:1, in accordance with a preferred aspect of the present invention.

TABLE 4

The release rates of CP from P&G, Complex of the invention and formulation compared at similar molar ratios.

| Formulation | Release rate (%/h) Mean ± s.e. (n = 5, 6) | P value compared to Formulation |
| --- | --- | --- |
| CP:ZnA (1:0.5) | | |
| P&G formulation | 0.657 ± 0.088 | P < 0.05 |
| Complex of the invention | 0.356 ± 0.040 | P < 0.05 |
| Formulation | 0.207 ± 0.025 | |
| CP:ZnA (1:1) | | |
| P&G formulation | 0 276 ± 0.045 | P < 0.05 |
| Complex of the invention | 0.221 ± 0.023 | P < 0.05 |
| Formulation | 0.140 ± 0.009 | |
| CP:ZnA (1:1.5) | | |
| P&G formulation | 0.182 ± 0.041 | P < 0.05 |
| Complex of the invention | 0.195 ± 0.016 | P < 0.05 |
| Formulation | 0.223 ± 0.020 | |
| CP:ZnA (1:2) | | |
| P&G formulation | 0.098 ± 0.026 | P < 0.05 |
| Complex of the invention | 0.108 ± 0.008 | P < 0.05 |
| Formulation | 0.245 ± 0.031 | |

Part 2

The results of this part are shown in Table 5 and FIG. 4. FIG. 4 shows the effect of CP release from P&G II, P&G IV, complex of the invention and formulation of the invention (CP:ZnA, 1:1 molar ratio) over time, mean±s.e (n=5, 6).

The results demonstrate that the rate of release of the P&G IV formulation was more than two-fold greater than P&G II formulation. Both of the P&G formulations were found to produce significantly greater CP release than the either the complex or the formulation of the invention. This data suggests that the release of CP through the cellulose ester membrane was enhanced when polyethylene glycol 400 in P&G II was replaced with ethanol (P&G IV) even at half the CP concentration.

TABLE 5

The release rates of CP from P&G, Complex of the invention and formulations.

| Formulation | Release rate (%/h) Mean ± s.e. (n = 5, 6) | P value compared to Formulation |
|---|---|---|
| P&G II | 0.276 ± 0.035 | P < 0.05 |
| P&G IV | 0.612 ± 0.050 | P < 0.05 |
| Complex of the invention (CP:ZnA, 1:1) | 0.221 ± 0.023 | P < 0.05 |
| Formulation of the invention (CP:ZnA, 1:1) | 0.140 ± 0.009 | |

Part 3

The results are shown in Table 6 and FIG. 5. FIG. 5 demonstrates the effect of the addition of water at 5, 15 and 40% to the P&G formulation at a Cp:ZnA 1:1.5 molar ratio, compared to complex and formulation of the invention (CP:ZnA, 1:1). The release rate of CP from the P&G formulation (at all water contents) was found to be significantly greater (p>0.05) than the formulations of the invention (CP:ZnA, 1:1), which provide longer duration of delivery, in accordance with a preferred aspect of the present invention.

TABLE 6

The effect of water on the release rates of CP from P&G (CP:ZnA, 1:1.5 molar ratio) compared to complex and formulation of the invention (CP:ZnA, 1:1)

| Formulation | Release rate (%/h) Mean ± s.e. (n = 5, 6) |
|---|---|
| CP:ZnA (1:1.5) | |
| P&G formulation (0% $H_2O$) | 0.182 ± 0.041 |
| P&G formulation (5% $H_2O$) | 0.301 ± 0.073 |
| P&G formulation (15% $H_2O$) | 0.435 ± 0.036 |
| P&G formulation (40% $H_2O$) | 0.672 ± 0.093 |
| CP:ZnA (1:1) | |
| Complex of the invention | 0.221 ± 0.023 |
| Formulation of the invention | 0.140 ± 0.009 |

From Example 2, at a CP:ZnA molar concentration of 1:1.5, the non-aqueous P&G formulation was found not to be significantly different (p>0.05) from the aqueous systems of the complex of the invention. Therefore, the addition of water to the P&G formulation would not be expected to alter the rate of release of CP from the P&G formulation. However, the release rate of CP was found to increase significantly, as the percentage of water was increased from 0% to 40%, suggesting that the release rate of CP from the P&G formulation is very much affected by water. Furthermore, the formulation of the invention contains approximately 40% water, but only has a release rate of approximately 20% of that of the P&G formulation (with a similar amount of water) indicating that the two formulations behave very differently.

Therefore, from the diffusion data observed, it could be concluded that both the formulations of the invention and P&G formulations behave very differently in terms of the mechanisms involved in the complexation of CP with Zn and the resultant effect on the thermodynamic activity of CP (drug release).

The invention claimed is:

1. A process for the preparation of an aqueous gel preparation comprising at least 30% by weight water together with a polymeric combination of clindamycin phosphate and a water-soluble $Zn^{2+}$ salt, the clindamycin phosphate being predominantly in Zwitterionic form with a deprotonated phosphate group and a protonated tertiary amine of the clindamycin phosphate, said Zwitterionic clindamycin phosphate being complexed to $Zn^{2+}$, the process comprising:
   providing a mixture of clindamycin phosphate with a liquid that includes at least 30% water by weight;
   adjusting the pH of the mixture to a pH above 7 and less than 8;
   adding a $Zn^{2+}$ salt to form said polymeric combination of zwitterionic clindamycin phosphate and $Zn^{2+}$.

2. The process according to claim 1 in which the mixture of clindamycin phosphate is provided with a liquid comprising water and a co-solvent.

3. The process according to claim 1, in which the pH of the mixture is adjusted to a pH between 7.0 and 7.5.

4. The process according to claim 2, wherein the co-solvent is ethanol in an amount of up to 70% by weight of the solvent mixture.

5. The process according to claim 4, wherein substantially equal amounts of water and ethanol are used.

6. The process according to claim 2, comprising substantially completely dissolving the clindamycin phosphate in the solvent mixture prior to adding the zinc salt.

7. The process according to claim 1, wherein the pH is adjusted by use of concentrated sodium hydroxide solution.

8. The process according to claim 5, wherein the co-solvent comprises a volatile, non-aqueous component and a non-volatile, non-aqueous component, and wherein the volatile, non-aqueous component forms between 10 and 50% of the total co-solvent, by weight.

9. The process according to claim 8, wherein the volatile, non-aqueous component is ethanol and the non-volatile, non-aqueous component is propylene glycol.

* * * * *

UNITED STATES PATENT AND TRADEMARK OFFICE
CERTIFICATE OF CORRECTION

PATENT NO.         : 8,268,790 B2                                    Page 1 of 1
APPLICATION NO.    : 12/574052
DATED              : September 18, 2012
INVENTOR(S)        : Emma Louise McDonagh et al.

It is certified that error appears in the above-identified patent and that said Letters Patent is hereby corrected as shown below:

On the Title Page, Item (54) and Column 1, line 1, "DERMATALOGICAL FORMULATIONS", should be -- DERMATOLOGICAL FORMULATIONS --.

On the Title Page, Item (57) ABSTRACT, line 1, "equimolor" should be -- equimolar --.

Column 1, after the title, insert the following heading: -- CROSS-REFERENCE TO RELATED APPLICATIONS --.

Column 20, lines 16 and 18, "Zwitterionic" should be -- zwitterionic --.

Column 20, line 42, "claim 5" should be -- claim 2 --.

Signed and Sealed this
Eleventh Day of December, 2012

David J. Kappos
*Director of the United States Patent and Trademark Office*